United States Patent [19]
Ameil et al.

[11] Patent Number: 6,077,263
[45] Date of Patent: Jun. 20, 2000

[54] VERTEBRAL OSTEOSYNTHETIC SYSTEM

[75] Inventors: Marc Ameil, Reims; Jean Huppert, L'Etrat; Jean-Louis Jermann, Chaumont; Thierry Marnay, Montpellier, all of France

[73] Assignee: Aesculap AG & Co. KG, Tuttlingen, Germany

[21] Appl. No.: 09/130,204

[22] Filed: Aug. 4, 1998

[30] Foreign Application Priority Data

Aug. 13, 1997 [FR] France .................................... 97 10327

[51] Int. Cl.⁷ .................................................. A61B 17/56
[52] U.S. Cl. ................................................................ 606/61
[58] Field of Search ................................ 606/60, 61, 79, 606/73, 59, 57, 69, 70, 71; 623/17

[56] References Cited

U.S. PATENT DOCUMENTS

| | | | |
|---|---|---|---|
| 5,498,263 | 3/1996 | DiNello et al. | 606/61 |
| 5,562,662 | 10/1996 | Brumfield et al. | 606/61 |
| 5,582,612 | 12/1996 | Lin | 606/61 |
| 5,702,393 | 12/1997 | Pfaifer | 606/61 |
| 5,702,395 | 12/1997 | Hopf | 606/61 |
| 5,716,355 | 2/1998 | Jackson et al. | 606/61 |

*Primary Examiner*—Michael Buiz
*Assistant Examiner*—(Jackie) Tan-Uyen T. Ho
*Attorney, Agent, or Firm*—Harrison & Egbert

[57] ABSTRACT

A spinal implant system including a spinal rod, a first clasp and a second clasp, a connecting element having a head and a shank connecting the first and second clasps, a first fastener for fastening the body of the first clasp to the spinal rod, a second fastener for fastening the shank of the connecting element to the body of the first clasp and a retainer for retaining the second clasp onto the head of the connecting element so that the second clasp can disengage itself from the head only in a direction toward the first clasp. The first clasp is adapted to be fixed to the vertebrae by a hook thereon. The second clasp is adapted to be fixed to the vertebrae by a hook thereon.

15 Claims, 3 Drawing Sheets

200

VERTEBRAL OSTEOSYNTHETIC SYSTEM

The invention presented here relates to spinal osteosynthetic surgery and, more precisely, to vertebral osteosynthetic systems, i.e. to those systems which are designed to immobilize at least two adjacent vertebra relative to each other.

Among these systems, the invention involves those which include at least one binding clip which is carried by a supporting instrument extending over at least one part of the spinal column. This supporting instrument can be a distraction or compression bar or a plate. The binding clamp is made up of two clasps which are designed to become fixed on either side of a vertebral projection, for example, a peduncle, a blade, or a transverse apophysis, of a same vertebra, and a connection component constructed to attach the two clasps to each other at least in the direction of their mutual extension.

BACKGROUND ART

Clips currently known, the connection component is made up of a screw in which the head is immobilized unidirectionally on one of the clasps and has a threaded shaft which is screwed into a tapped bore of the body of the other clasp. A locking screw is screwed into this body, transversally to the threaded shaft, in order to immobilize the connection screw relative to it.

A binding clip of this type is of the automatic stable type, in the sense that it can be placed on a vertebra in a stable manner due to the fact that the two clasps are fixed on the vertebra and held in place by the connection screw, while the support instrument is not yet in place.

On the other hand, this binding clip presents a disadvantage which lies in the fact that the user must work successively on two screws, i.e. the connection screw and the locking screw. In so far as the connection screw is concerned, the user must, on the one hand, perfectly align this screw with the threaded body and, on the other hand, for the proper threaded joint, must have recourse to a complex instrument of the cardan drive screwdriver type, which is less convenient. On the other hand, in so far as the locking screw is concerned, it is more approachable and ensures a good transverse locking of the connection component by tightening.

In addition, due to the fact that a connection screw is used, these binding clips are cumbersome and bulky in height, which limits their use.

SUMMARY OF THE INVENTION

The goal of correcting these disadvantages while keeping the advantages of a locking screw and, for this purpose, the binding clip according to the invention is characterized in that the connection component includes a shaft which has a first end immobilizable in at least one direction on one of the clasps and a shank immobilizable on the other clasp; the aforementioned other clasp having an extended receptacle for receiving the shank, this receptacle being open at its two ends and opening out transversally to the outside over its entire length between the two opposing surfaces to allow a positioning and a removal at the side of the connection component relative to the other clasp; and a locking screw of the shank is formed in the receptacle, the axis of which is perpendicular to the longitudinal direction of the receptacle and which acts together with a tapped hole installed on the opposing surfaces.

Thus, in the binding clip according to the invention, a shaft which is threaded without a threaded joint in a receptacle, either axially, or on the side, is used as the connection component. This shaft is locked in position by the locking screw, and relatively easy to access and manipulate. The control of the relative position of the two clasps is done by the simple sliding of the connection shaft relative to one of the clasps, the locking in a selected position being done using the locking screw. In the system according to the invention, it is not necessary to maneuver a screw as the connection component.

According to a preferred embodiment mode, the receptacle is combined with one of the clasps which is carried by the support instrument.

The surface of the shank of the connection component is smooth or has, at least in the area of the second end of the connection shaft acting together with the receptacle, roughness, for example, a knurling, striations, or notches.

The axis of the locking screw can be oblique or perpendicular with respect to the plane defined by the parallel axes of the support instrument and the connection shaft.

The receptacle can have a bottom having a semi-circular cross section, corresponding to the diameter of the shank of the connection component, extended towards the outside by the two opposing surfaces which are preferably parallel.

One of the two clasps which is carried by the support instrument can have a split threaded head for the reception of the support instrument which is immobilized there by the nut. This nut, the receptacle and the locking screw are preferably constructed so that the nut prevents an untimely exit of the locking screw, which would unlock the connection shaft. For example, the nut is supported on the locking screw.

The first end of the connection component, which is fixed in at least one direction on one of the clasps, has a cylindrical or conical head which is received in a complementary receptacle provided in the clasp which carries it and can be stopped against a shouldering wall.

The receptacle for receiving the connection shaft can be arranged in the body itself of the other clasp, or even in a collar which is held united with the other clasp.

In the second case, this other clasp has, in an advantageous manner, a supporting shoulder of the collar.

This collar preferably has an axial plane of symmetry which allows its mounting, and therefore, the mounting of the clasp that it carries, using the connection component, both to the right and to the left of the support instrument, and of the clasp with which it acts directly.

This collar can have two opposing and aligned indentations which extend the slot of the head of the clasp to receive and support the support instrument.

BRIEF DESCRIPTION OF THE DRAWINGS

Be understood well in reading the supplemental description which follows, of two preferred embodiment modes of the invention, and by referring to the attached drawings which make up a part of the description and in which.

DETAILED DESCRIPTION OF THE INVENTION

Figure 1:
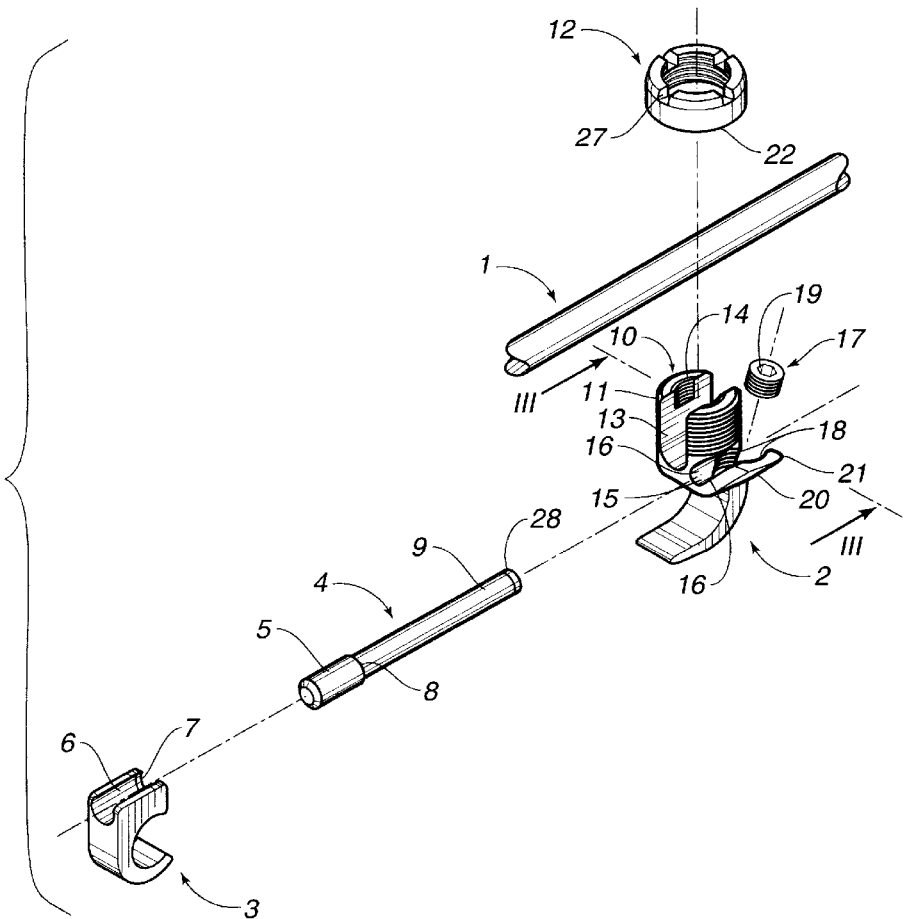
FIG. 1 is an exploded perspective view showing the pieces making up a binding clip constructed according to a first preferred embodiment mode of the invention, connected to a support bar.

In reference to the FIGS. 1 to 6 are the common characteristics of the two preferred embodiment modes.

The binding clip according to the invention is designed to be fixed on a vertebra (not shown), by a peduncle, a blade, or a transverse apophysis of the vertebra, to immobilize it with respect to at least one other vertebra using a support instrument 1, here a distraction or compression bar.

In order to fix it onto the vertebra, the binding clip includes, as shown best in FIGS. 1, 4, 5 and 6, two clasps, i.e. one main clasp 2 and an auxiliary or counter-clasp 3, which are open towards each other and are connected to themselves, in at least one direction, i.e. in the direction of their mutual extension, by a connection component 4. Thus, the clasps 2 and 3 can be fixed on either side of the accommodated vertebral projection, by being held there by the connection component 4.

This connection component 4 includes a shaft which has an end or head 5 constructed in order to be immobilized in at least the direction indicated by the arrow A (FIG. 2) on the counter-clasp 3. The head 5 is indicated in the form of a cylinder designed to be received in a cylindrical receptacle 6 of the counter-clasp 3. The receptacle 6 is open to the top and it extends over more than 180° in order to be able to transversally hold the head 5 of the shaft 4. The axial restraint of the head 5 is ensured by a shoulder 7 positioned at the end of the receptacle 6, on the side facing the main clasp 2. This shoulder 7 is designed to act together with the base 8 of the head 5. This base also has a connection shoulder with the shank 9 of the shaft 4. This shaft 4 has a diameter less than that of the head 5. The angular range of the receptacle 6 is such that the shaft 4 can be engaged in the receptacle 6, either axially or transversally, after which the shaft 4 is displaced axially according to the arrow A of FIG. 2, so that when the head 5 enters the receptacle 6, its base 8 is stopped against the shoulder 7, and the shaft 4 being thus unified with the counter-clasp 3 both transversally as well as in the direction of the arrow A. As a variation, the receptacle 6 and the head 5 can be conical, becoming slimmer going towards the shank 9, the shoulder of the stop 7 thus no longer being necessary.

The main clasp 2, which is designed to receive the bar 1, has a cylindrical head 10 with external threads 11, for the reception of a nut 12, and, roughly over its entire height, a diametrical slot 13 having a size corresponding roughly to the diameter of the bar 1 for receiving it. This being the case, on the sides of the slot 13, the head 10 can have a tapped hole 14 for receiving a mounting tool.

The main clasp 2 has an extended receptacle 15 for receiving the shank 9 of the connection component 4. This receptacle 15 is open at its two ends and opens transversally to the outside over its entire length between the two opposing surfaces 16 in order to allow the positioning and removal at the side, of the connection component 4 relative to the clasp 2. A locking screw 17 acts together with the two threaded portions of a tapped hole 18 arranged on its surfaces 16. The locking screw 17 does not have a head and it has a hexagonal operating recess 19.

In general, the shank 9 of the connection component 4 is cylindrical and has a circular cross section; in this case, the receptacle 15 has a base with semi-circular cross section having a radius corresponding to that of the shank 9. The bottom of the receptacle 15 is extended towards the outside by the two opposing surfaces 16, which are preferably parallel.

The surface of the shank 9 of the connection component 4 can be either smooth or has, at least in the area which is located at its free end and which acts together with the receptacle 15 and the locking screw 17, roughness, for example, a knurling, striations, or notches, encouraging the support of the shank by friction when the screw 17 is tightened.

The assembly is constructed such that when the connection component 4 is in its receptacle 15 and is fixed there by the locking screw 17, and when the support instrument 1 is in the diametrical slot 13 of the cylindrical head 10, the nut 12 fixes the support instrument 1 in the head 10 and, simultaneously, rests on the locking screw 17 in order to prevent an untimely exit of the nut by unscrewing.

Figure 3:
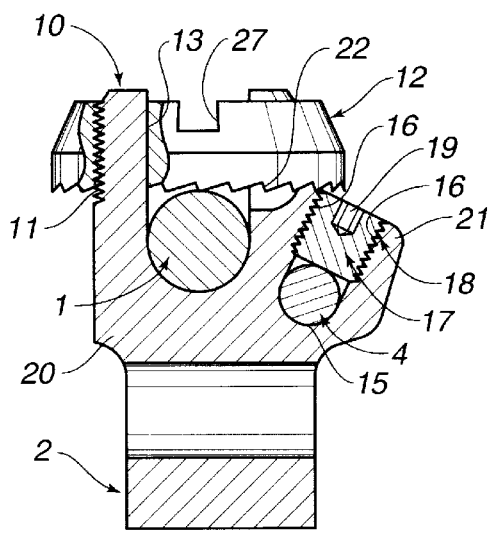
FIG. 3 is, on a larger scale, an axial section along the line III—III of FIG. 1, with a cut-away, showing the binding clip in the assembled mounted state on the support instrument.
Figure 6:
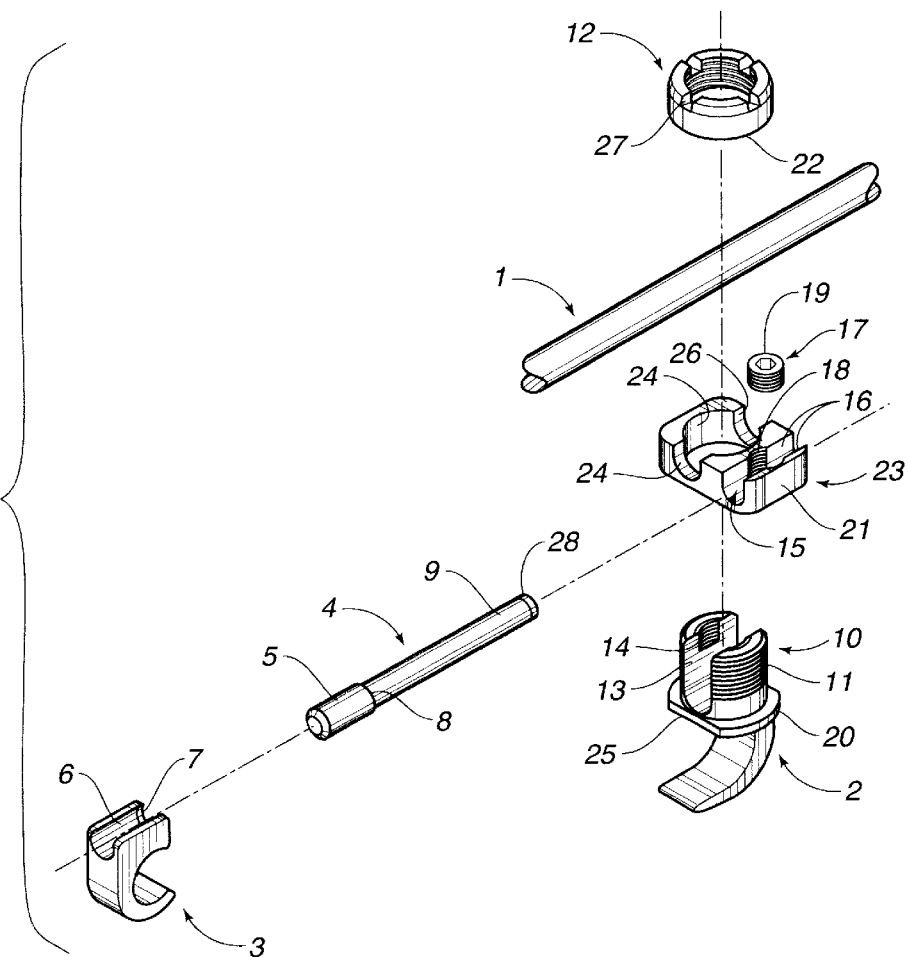
FIG. 6 is an exploded perspective view similar to FIG. 1, showing the pieces making up a binding clip constructed according to a second preferred embodiment mode of the invention, connected to a support bar.

As shown in FIGS. 1 and 3, the axis of the locking screw 17 can be inclined with respect to the axis of the head 10 of the clasp 2. However, as shown in FIG. 6, the axis of the screw 17 can be parallel to the axis of the head 10 of the clasp 2. Moreover, the axis of the locking screw 17 can be either perpendicular (FIGS. 1 and 3) or crosswise (FIG. 6) with respect to the plane defined by the parallel axes of the support instrument 1 and the connection component 4.

Now the characteristics peculiar to the embodiment mode of FIGS. 1 to 5 will be described.

In this embodiment, the extended receptacle 15, which is parallel to the base of the diametrical slot 13 of the head 10, is formed directly in the body 20 of the clasp 2. This body 20 has an inclined edge 21 in projection allowing the definition of one of the surfaces 16 extending the base of the receptacle 15 to the outside.

Figure 4:
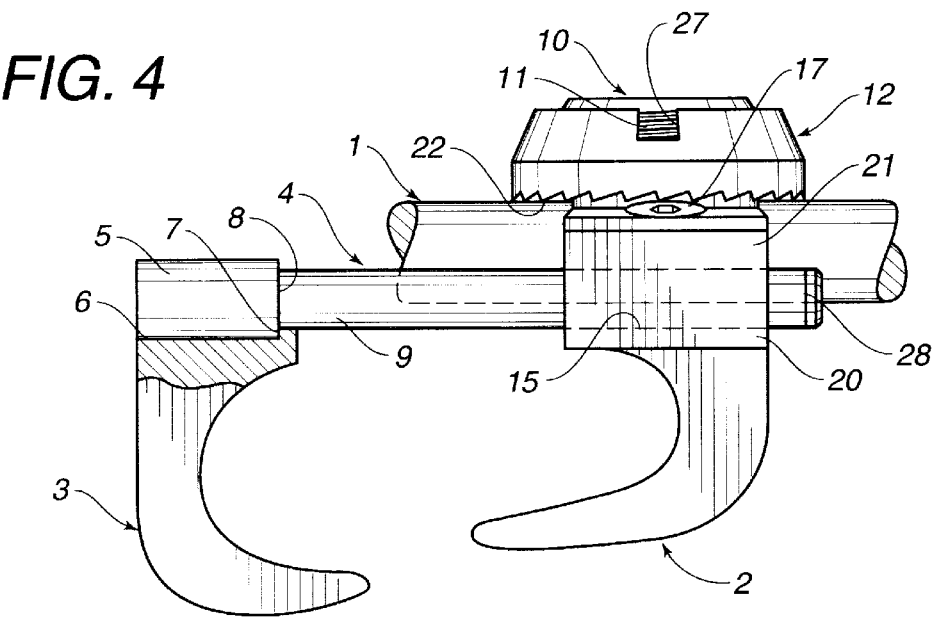
FIG. 4 is a lateral cut-away view of the binding clip and the support instrument in the assembled state.
Figure 5:
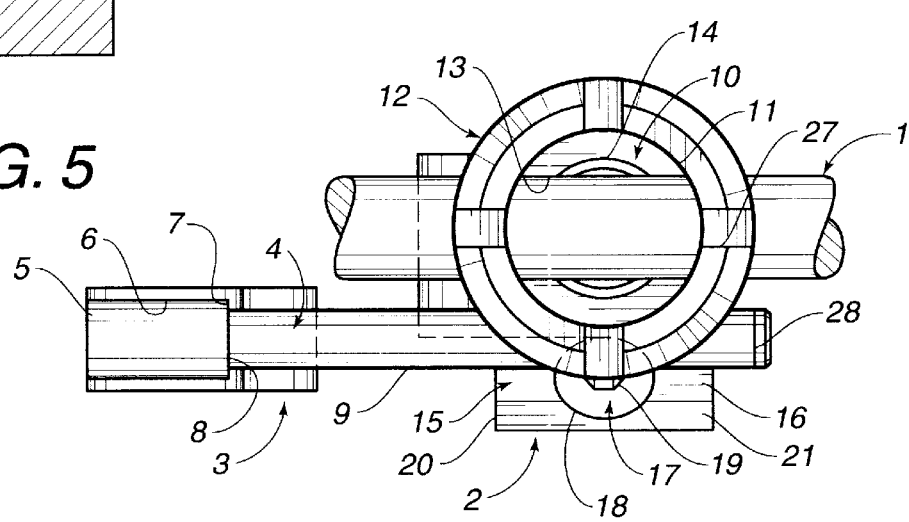
FIG. 5 is a planar view of the binding clip and the support instrument in the assembled state.

As shown in FIGS. 3 to 5, when the shank 9 of the connection component 4 is immobilized in the base of the receptacle 15 by the locking screw 17 and the support instrument 1 is located at the base of the diametrical slot 13, in parallel relation to the shank 9, the nut 12, equipped with notches 22, simultaneously rests on the support instrument 1 and on the free outside end of the locking screw 17 in order to ensure both the immobilization of the support instrument 1 and the locking of the locking screw 17, and therefore, of the connection component 4.

Now the characteristics peculiar to the embodiment mode of FIG. 6 will be described.

In this embodiment, the receptacle 15 is arranged, not in the body 20 of the clasp 2, but in a separate collar 23 designed to be immobilized on the body of the clasp 2 by the nut 12. This collar is of a generally rectangular appearance, and it has a central bore 24 for its mounting without play on the head 10 of the main clasp 2. The receptacle 15 rests on a shoulder 25 formed on the head 10 integrally with the body 20. The front of the collar 23 which is opposed to the support face on the shoulder 25 has two indentations 26 opposed and aligned which open into the central bore 24 and which are aligned with the sides of the diametrical slot 13 of the head 10. These indentations have a semi-circular configuration with a radius, equal to that of the bar 1. Due to the fact that the slot 13 of the head 10 extends roughly axially to the shoulder 25, the bar 1 is supported on the bottom of the indentations 26 and, transversally, it is in contact with the sides of the slot 13, which prevents rotation of the collar.

In order to receive the shank 9 of the connection component 4, the collar 23 is set eccentrically with respect to its central bore 24, and the receptacle 15 is arranged with its eccentric part parallel to the indentations 26.

The collar 23 has an axial plane of symmetry, perpendicular to the axis of the receptacle 15.

The assembly is constructed such that after assembly the nut 12 rests simultaneously on the support instrument 1 and on the locking screw 17, without contact with the collar 23. The nut 12 can have notches 22 on its threaded face. By resting on the support instrument 1, it pins the support instrument in the notches 26, which pushes the collar 23 against the shoulder 25; at the same time, it rests on the locking screw 17, while preventing its untimely exit by unscrewing.

With respect to the embodiment mode of FIGS. 1 to 5, the embodiment mode of FIG. 6 requires a supplementary piece, i.e. the collar 23, but it has the advantage of allowing a positioning of the connection component 4, and therefore, of the counter-clasp 3, to the left or to the right with respect to the main clasp 2, and this is due to the fact that the collar 23 can take up two positions 180° apart.

Figure 2:
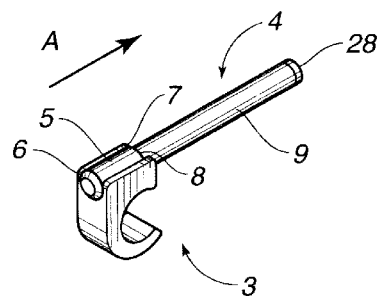
FIG. 2 is a perspective view showing only the connection component mounted on one of the clasps.

In order to position the binding clip, prior to positioning the support instrument 1, the connection component 4 and the counter-clasp 3 are assembled, as shown in FIG. 2, and the shank 9 of the connection component 4 is placed in the receptacle 15, either axially, or transversally, due to the fact that the receptacle 15 is open on the side along its entire length. The clasps 2 and 3 are then placed on either side of the vertebral projection involved, this positioning is accompanied by a free sliding of the shank 9 in the receptacle 15. For this positioning, the user can, for example, use a compression binding clip, the jaws of which take hold on the back of the clasp 3 and on a notch, groove, or the like 28 formed at the free end of the shank 9. After the desired position of the clasps has been obtained, they are locked in place by screwing the locking screw 17. Thus, one obtains a stable mounting of the two clasps on the vertebral projection, even though the support instrument 1 is not yet in place.

Later, after the placement by the user of other components for affixing on the spinal column, the support instrument 1 can be put in place and then immobilized by its penetration in the slot 13 of the main clasp 2 and the indentations 26 of the collar 23, after which the nut 12 is screwed on, for example, using a gripping tool acting together with the notches 27 arranged on the nut 12.

When the nut 12 is screwed in, this nut is supported on the support instrument 1 in order to lock against the bottom of the indentations 26 and, at the same time, it rests on the locking screw 17.

Of course, the invention is not limited to the embodiment modes which have been described; on the contrary, different variations can be conceived without necessarily leaving its frame. The foregoing disclosure and description of the invention is illustrative and explanatory thereof. Various changes in the details of the illustrated apparatus may be made within the scope of the appended claims without departing from the true spirit of the invention. The present invention should only be limited by the following claims and their legal equivalents.

What is claimed is:

1. A spinal implant system comprising:

a spinal rod;

a first clasp and a second clasp having respectively a first and a second body and a first and a second hook, said first clasp being adapted to be fixed to a vertebrae by said first hook and said second clasp being adapted to be fixed to the vertebrae by said second hook;

a connecting element comprising a head and a shank, said connecting element connecting said first and second clasps;

a first fastening means for fastening said first body to said spinal rod;

a second fastening means for fastening said shank to said first body; and a retaining means for retaining said second clasp onto said head so that said second clasp, in the retaining position, can disengage itself from said head only in a direction toward said first clasp, said first body defining a recess for reception of said shank, said recess having a bottom and two lateral walls, said recess defining first and second lateral openings and an upper opening, said bottom being on a side of said first hook, said upper opening being on a side opposite to said first hook such that said connecting element can be inserted and removed through said upper opening, said second fastening means having a blocking screw for blocking said shank in said recess, said blocking screw having a screwing axis perpendicular to said shank and cooperative with a tapped hole formed in said two lateral walls.

2. The spinal implant system according to claim 1, wherein a surface of said shank is smooth.

3. The spinal implant system according to claim 1, wherein said shank has a roughened surface adjacent an end thereof.

4. The spinal implant system according to claim 1, wherein said screwing axis of said blocking screw is oblique or perpendicular with respect to a plane defined by parallel axes of said spinal rod and said connection shaft.

5. The spinal implant system according to claim 1, wherein said bottom is of a semi-circular cross section and corresponds to a diameter of said shank of said connecting element.

6. The spinal implant system according to claim 1, wherein said first clasp has a split threaded head for receiving said spinal rod, said split threaded head having a nut threadedly received therein for immobilizing said spinal rod.

7. The spinal implant system according to claim 6, wherein said nut, said recess and said blocking screw are constructed to prevent an exit of said blocking screw.

8. The spinal implant system according to claim 7, wherein said nut is supported on said blocking screw.

9. The spinal implant system according to claim 6, wherein said screwing axis of said blocking screw is parallel to or oblique with respect to an axis of said split threaded head.

10. The spinal implant system according to claim 1, wherein said head of said connecting element comprises a cylindrical or conical head which is received in a complementary receptacle provided in the respective clasp.

11. The spinal implant system according to claim 1, wherein said recess is formed in a base of the first clasp.

12. The spinal implant system according to claim 1, wherein said recess is formed in a collar which is held attached to said first clasp.

13. The spinal implant system according to claim 12, wherein said first clasp has a shoulder supporting said collar.

14. The spinal implant system according to claim 12, wherein said collar has two opposing and aligned indentations which are aligned with a slot in said head to receive and support said spinal rod.

15. The spinal implant system according to claim 12, wherein said collar has an axial plane of symmetry which allows a mounting of said second clasp using said connecting element.

* * * * *